(12) United States Patent
Allegrini et al.

(10) Patent No.: US 6,998,490 B2
(45) Date of Patent: Feb. 14, 2006

(54) PROCESS FOR THE PREPARATION OF ORGANIC COMPOUNDS CONTAINING A SULFINYL OR SULFONYL GROUP

(75) Inventors: Pietro Allegrini, San Donato Milanese (IT); Caterina Napoletano, Laveno Mombello (IT); Gabriele Razzetti, Sesto S. Giovanni (IT); Graziano Castaldi, Briona (IT)

(73) Assignees: Dinamite Dipharma S.p.A., Mereto Di Tomba (IT); Abbreviated Dipharma S.p.A., Mereto Di Tomba (IT)

( * ) Notice: Subject to any disclaimer, the term of this patent is extended or adjusted under 35 U.S.C. 154(b) by 44 days.

(21) Appl. No.: 10/801,608

(22) Filed: Mar. 17, 2004

(65) Prior Publication Data

US 2004/0192929 A1    Sep. 30, 2004

(30) Foreign Application Priority Data

Mar. 28, 2003  (IT)  .......................... MI2003A0617

(51) Int. Cl.
*C07C 317/02*  (2006.01)
(52) U.S. Cl. .................... 548/366.1; 564/162; 568/27; 568/28
(58) Field of Classification Search ............ 548/366.1; 564/162; 568/27, 28
See application file for complete search history.

(56) References Cited

U.S. PATENT DOCUMENTS

| | | | | | |
|---|---|---|---|---|---|
| 3,210,243 A | * | 10/1965 | Goodhue et al. | ............ | 514/708 |
| 3,492,316 A | * | 1/1970 | Adams et al. | ............... | 549/556 |
| 3,647,858 A | * | 3/1972 | Hinkley et al. | ................ | 560/11 |
| 4,670,470 A | | 6/1987 | Firestone | | |
| 5,413,733 A | * | 5/1995 | Nicholson et al. | ...... | 252/186.42 |
| 5,429,769 A | * | 7/1995 | Nicholson et al. | .......... | 510/376 |
| 5,480,577 A | * | 1/1996 | Nicholson et al. | .......... | 510/372 |
| 5,633,223 A | * | 5/1997 | Vasudevan et al. | ......... | 510/303 |
| 5,672,295 A | * | 9/1997 | Gary et al. | ............ | 252/186.42 |

FOREIGN PATENT DOCUMENTS

EP          0 325 288 A       7/1989

* cited by examiner

*Primary Examiner*—Johan Richter
*Assistant Examiner*—Chukwuma Nwaonicha
(74) *Attorney, Agent, or Firm*—Arent Fox PLLC

(57) ABSTRACT

A process for the oxidation of thioethers to sulfoxides or sulfones or for the oxidation of sulfoxides to sulfones by treatment of thioethers or sulfoxides with an oxidizing amount of ε-phthalimidoperhexanoic acid is particularly useful for the preparation of compounds of industrial interest, in particular pharmaceuticals for human or veterinary use.

10 Claims, No Drawings

PROCESS FOR THE PREPARATION OF ORGANIC COMPOUNDS CONTAINING A SULFINYL OR SULFONYL GROUP

FIELD OF THE INVENTION

The present invention relates to an oxidation process for the preparation of sulfinyl- or sulfonyl-organic compounds, useful as biologically active compounds or as intermediates in their preparation.

TECHNOLOGICAL BACKGROUND

A number of compounds of industrial interest, in particular pharmaceuticals for human or veterinary use, contain a sulfinyl or sulfonyl group. Their synthesis usually comprises an oxidation step wherein a thioether intermediate (—S—) is transformed into a sulfinyl (—SO—) or sulfonyl (—SO$_2$—) compound. Different oxidizing agents are available for this oxidation, such as those described by S. Uemura in "Comprehensive Organic Synthesis", chapter 6.2, edited B. M. Trost and J. Fleming, Pergamon Press (1991). Nevertheless, only some of these oxidizing agents are suitable for industrial application, due to the fact that they are not easily available on the market, to environment-safety and hygiene problems related to their use, or to their poor chemical selectivity. Among those suitable for industrial use, hydrogen peroxide and sodium hypochlorite are usually preferred, as they are commercially available in large amounts and at low cost. However, it is known that the use of hydrogen peroxide on an industrial scale is hazardous, as reported in "Handbook of Chemical Hazards", E. Brewtherick and Butterworths (1979). Moreover, the oxidation of organic compounds with hydrogen peroxide is very often carried out in the presence of catalysts based on transition metals, such as tungstenum, titanium, vanadium and molybdenum. The removal of these catalysts from the reaction product is recognizedly troublesome, as it requires additional purification steps with consequent increase in production costs and decrease in yield.

In general, the oxidizing power of sodium hypochlorite is not sufficient to obtain sulfonyl derivatives. Moreover, in most cases the oxidation of thioethers with sodium hypochlorite is not sufficiently selective and leads to undesired by-products.

A known medicament that contains a sulfinyl group is modafinil, i.e. 2-[(diphenylmethyl)sulfinyl]acetamide. According to various synthetic methods, intermediate 2-[(diphenylmethyl)thio]acetic acid or 2-[(diphenylmethyl)thio]acetamide is oxidized with hydrogen peroxide to give 2-[(diphenylmethyl)sulfinyl]acetic acid, or 2-[(diphenylmethyl)sulfinyl]acetamide, respectively. This oxidation, usually performed with 110 volumes hydrogen peroxide, involves safety problems. Similar problems also occur in the synthesis of other biologically active sulfinyl compounds, such as sulindac, i.e. (Z)-5-fluoro-2-methyl-1-[[4-(methylsulfinyl)phenyl]methylene]-1H-indene-3-acetic acid, and the so-called "prazoles", i.e. [[(pyridyl)methyl]sulfinyl]benzimidazole derivatives, which are known anti-secretory agents.

There is therefore still the need of a further cheap oxidizing agent that allows to operate safely and to easily control the reaction, so as avoid formation of by-products, such as N-oxides and/or sulfonyl derivatives, also satisfies the requirements of regulatory authorities. These requirements are particularly strict for pharmaceutical products, wherein the said by-products should be present in the lowest amount.

It has now been found that the oxidation of a thioether group to a sulfinyl (sulfoxide) or sulfonyl (sulfone) group can be advantageously carried out using ε-phthalimidoperhexanoic acid as the oxidizing agent. In particular, it has been found that ε-phthalimidoperhexanoic acid can be easily and safely handled and used on an industrial scale without the need of particular plants or specific safety procedures. Moreover, ε-phthalimidoperhexanoic acid and its reduced by-product, ε-phthalimidohexanoic acid, are substantially low polluting and can be advantageously used on a large scale.

ε-Phthalimidoperhexanoic acid is a stable, commercially available, solid and cheap product, used for the preparation of cosmetic formulations and detergents for domestic or industrial use.

DETAILED DISCLOSURE OF THE INVENTION

The present invention relates to a process for the oxidation of thioethers to sulfoxides or sulfones or for the oxidation of sulfoxides to sulfones by treatment of thioethers or sulfoxides with an oxidizing amount of ε-phthalimidoperhexanoic acid.

The process of the invention is particularly useful for the preparation of biologically active compounds containing sulfinyl or sulfonyl groups, such as modafinil; modafinil-sulfone (i.e. modafinil sulfonyl analogue); sulindac; sulindac-sulfone (i.e. sulindac sulfonyl analogue); dapsone; and [[(pyridyl)methyl]sulfinyl]benzimidazole derivatives, known as anti-secretory agents, such as those disclosed in WO 01/04109 and EP 998944, in particular:

omeprazole, i.e. (5-methoxy-2[[(4-methoxy-3,5-dimethyl-2-pyridinyl)methyl]sulfinyl]-1H-benzimidazole);

pantoprazole, i.e. (5-difluoromethoxy-2[[3,4-dimethoxy-2-pyridinyl)methyl]sulfinyl]-1H-benzimidazole);

lansoprazole, i.e. (2-[[[methyl-4-(2,2,2-trifluoroethoxy)-2-pyridinyl]methyl]sulfinyl]-1H-benzimidazole];

timoprazole, i.e. (2-[[(2-pyridinyl)methyl]sulfinyl]-1H-benzimidazole);

picoprazole, i.e. (5-ethoxycarbonyl-6-methyl-2[[(3-methyl-2-pyridinyl)methyl]sulfinyl]-1H-benzimidazole);

rabeprazole, i.e. (2-[[[3-methyl-4-(3-methoxypropoxy)-2-pyridinyl]methyl]sulfinyl]-1H-benzimidazole);

exomeprazole, i.e. the (S)-isomer of omeprazole.

Intermediate compounds containing a thioether group are, for example:

intermediates for the preparation of sulindac, in particular those disclosed in U.S. Pat. No. 3,647,858, such as 1-(4-fluorophenyl)-2-(4-methylthio-phenyl)-ethanone and (Z)-5-fluoro-2-methyl-1-[[4-(methylthio)-phenyl]methylene]-1H-indene-3-acetic acid; preferably (Z)-5-fluoro-2-methyl-1-[[4-(methylthio)-phenyl]methylene]-1H-indene-3-acetic acid;

intermediates for the preparation of modafinil, such as 2-[(diphenylmethyl)thio]acetic acid and 2-[(diphenylmethyl)thio]acetamide;

intermediates for the preparation of dapsone, such as 4,4'-thiobisbenzenamine;

intermediates for the preparation of [[(pyridyl)methyl]sulfinyl]benzimidazoles, i.e. [[(pyridyl)methyl]thio]benzimidazole derivatives having the following structure:

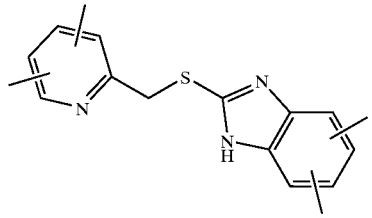

such as:
(5-methoxy-2[[(4-methoxy-3,5-dimethyl-2-pyridinyl)methyl]thio]-1H-benzimidazole);
(5-difluoromethoxy)-2-[(4-chloro-3-methoxy-2-pyridinyl)methyl]thio-1H-benzimidazole;
(5-difluoromethoxy-2[[3,4-dimethoxy-2-pyridinyl)methyl]thio]-1H-benzimidazole);
(2-[[[methyl-4-(2,2,2-trifluoroethoxy)-2-pyridinyl]methyl]thio]-1H-benzimidazole];
(2-[[(2-pyridinyl)methyl]thio]-1H-benzimidazole);
(5-ethoxycarbonyl-6-methyl-2[[(3-methyl-2-pyridinyl)methyl]thio]-1H-benzimidazole);
(2-[[[3-methyl-4-(3-methoxypropoxy)-2-pyridinyl]methyl]thio]-1H-benzimidazole); and
(S) (5-methoxy-2[[(4-methoxy-3,5-dimethyl-2-pyridinyl)methyl]thio]-1H-benzimidazole).

Examples of intermediate compounds containing a sulfinyl group are sulindac, modafinil, 1-(4-fluorophenyl)-2-(4-methylsulfinyl-phenyl)-ethanone, and 2-[(diphenylmethyl)sulfinyl]acetic acid.

The oxidation can be carried out by reacting the substrate with ε-phthalimidoperhexanoic acid in an organic solvent or mixtures thereof. The reaction temperature typically ranges from −20° C. to the reflux temperature of the solvent, in particular from about 0 to 40° C., and the reaction time ranges typically from 0.5 to 24 hours, preferably from about 1 to 2 hours.

According to a preferred aspect of the invention, to oxidize a compound containing a thioether group to a compound containing a sulfoxy group, or to oxidize a compound containing a sulfoxy group to a compound containing a sulfonyl group, the amount of ε-phthalimidoperhexanoic acid ranges typically from about 0.8 to 1.5 equivalents, preferably from 0.9 to 1 equivalents, per equivalent of substrate.

To oxidize a compound containing a thioether group to a compound containing a sulfonyl group, the oxidizing agent is used in amounts ranging from about 1.5 to 3 equivalents, preferably from 1.9 to 2.1 equivalents per equivalent of substrate.

The organic solvent can be a water-miscible or immiscible, aprotic or protic organic solvent.

Examples of solvents are aliphatic chlorides, in particular methylene chloride, chloroform, carbon tetrachloride, trichloroethane, tetrachloroethylene, preferably methylene chloride; aromatic chlorides, in particular chlorobenzene and ortho-dichlorobenzene, the latter being preferred; aromatic hydrocarbons, in particular benzene, ortho-, meta-, para-xylene and toluene, the latter being preferred; carboxylic acid esters, in particular methyl-, ethyl-, propyl-, isopropyl-, butyl- and isobutyl acetate, preferably ethyl acetate; alkyl carbonates, for example dimethyl carbonate; alkanols, preferably $C_1$–$C_5$ alkanols, for example methanol, ethanol, propanol, iso-propanol, n-butanol, sec-butanol and tert-butanol, in particular iso-propanol; alkyl ketones and cycloalkyl groups, for example acetone, methyl ethyl ketone, methyl isobutyl ketone and cyclohexanone. Preferred solvents are $C_1$–$C_5$ alkanols, in particular methanol, iso-propanol and tert-butanol, and aliphatic chlorides, in particular dichloromethane.

Any groups possibly interfering with the oxidation can be protected before the reaction and subsequently deprotected according to known methods. If the final compounds exist in more isomeric forms, they can be obtained as mixtures or separated according to conventional methods.

The use of ε-phthalimidoperhexanoic acid allows to monitor the oxidation kinetics, so as to avoid the formation of by-products having different oxidation degree and/or dangerous accumulations of the oxidizing agent, which occur, on the contrary, with the use of other known oxidizing agents, for example the aqueous solution of peracetic acid/hydrogen peroxide/acetic acid, which contains about 15% of active oxygen. Therefore, the process of the invention can be easily carried out on large scale without particular risks.

Moreover, the physico-chemical properties of ε-phthalimidohexanoic acid, the by-product of the oxidation reaction, allow to easily recover the final product. This is of utmost importance in the case of biologically active compounds, as they are obtained in highly pure form, without the need of troublesome and costly purification processes. ε-Phthalimidohexanoic acid is soluble in aqueous alkali solutions, such as solutions of alkali or alkaline-earth metals hydroxides, in particular sodium or potassium hydroxide, ammonium hydroxide or monomethylamine. Therefore, when the oxidation is carried out in a water-immiscibile organic solvent, ε-phthalimidohexanoic acid can be removed from the reaction mixture by simple washing with an aqueous alkali solution. Instead, when the oxidation is carried out in a solvent in which ε-phthalimidohexanoic acid is soluble, for example one of the above-indicated protic solvents, the resulting sulfinyl or sulfonyl compound can be recovered by crystallisation from the reaction mixture.

The following examples illustrate the invention.

EXAMPLE 1

Preparation of (5-difluoromethoxy)-2-[(4-chloro-3-methoxy-2-pyridinyl)methyl]sulfinyl-1H-benzimidazole (intermediate for the preparation of pantoprazole)

5-Difluoromethoxy-2-[(4-chloro-3-methoxy-2-pyridinyl)methyl]thio-1H-benzimidazole (50 g) and isopropyl alcohol (150 ml) are loaded in a 1000 ml round-bottom flask. The resulting whitish-beige suspension, thermostated at 20° C.±5° C., is added dropwise with a solution of ε-phthalimidoperhexanoic acid (70% w/w; 50.64 g) in isopropyl alcohol (150 ml), kept at about 40° C. to avoid crystallisation of ε-phthalimidoperhexanoic acid, in 45÷90 minutes. The reaction is exothermic: a temperature increase of about 10° C. is observed and the addition rate has to be adjusted so that the temperature decreases between successive additions. The reaction mixture progressively dissolves and turns orange. At the end of the addition the solution is allowed to cool to room temperature. According to the reaction kinetics, monitored by H.P.L.C. (% area), the oxidizer enters and reacts without giving rise to any dangerous accumulation. In fact, upon additions amounting to 25%, 50% or 75% of the oxidizing agent, a proportional conversion in the final product is observed. At the end of the addition the formation of the product is almost complete, maximal conversion being achieved after 1 hour. At the end of the addition an orange solution is obtained; crystallisation starts after about 1 hour.

5 Hours after the end of the addition, the oxidizer is completly consumed, and 2 ml of 0.1M $Na_2SO_3$ aqueous solution are added as a precaution. Thereafter, 225 ml of water are added, to promote maximal precipitation of the product, stirring for 24÷48 hours at room temperature.

The product is filtered at 20±5° C., washing with a 1/1 alcohol isopropyl/water mixture and dried in a vent static dryer at room temperature. 44 g of (5-difluoromethoxy)-2-[(4-chloro-3-methoxy-2-pyridinyl)methyl]sulfinyl-1H-benzimidazole is obtained, as a compact, white solid. (Molar yield 88.8%).

HPLC purity=99.7%; HPLC titer=100%; K.F.=0.4%; Residue on ignition=0.5%.

The mother liquor is clear, dark orange, and HPLC (purity %) reveals that it contains ε-phthalimidohexanoic acid (44%), sulfone (14.4%), sulfoxide (25.2%), sulfide (12.4%) and other compounds (4%). The residue obtained through evaporation of the solvent under reduced pressure has HPLC purity amounting to 6.4% as sulfoxide.

Using the same procedure, the following compounds can be prepared:
  omeprazole from (5-methoxy-2[[(4-methoxy-3,5-dimethyl-2-pyridinyl)methyl]thio]-1H-benzimidazole);
  pantoprazole from (5-difluoromethoxy)-2-[(3,4-dimethoxy-2-pyridinyl)methyl]thio-1H-benzimidazole;
  lansoprazole from (2-[[[methyl-4-(2,2,2-trifluoroethoxy)-2-pyridinyl]methyl]thio]-1H-benzimidazole];
  timoprazole from (2-[[(2-pyridinyl)methyl]thio]-1H-benzimidazole);
  picoprazole from (5-ethoxycarbonyl-6-methyl-2[[(3-methyl-2-pyridinyl)methyl]thio]-1H-benzimidazole);
  rabeprazole from (2-[[[3-methyl-4-(3-methoxypropoxy)-2-pyridinyl]methyl]thio]-1H-benzimidazole); and
  exomeprazole from (S) (5-methoxy-2[[(4-methoxy-3,5-dimethyl-2-pyridinyl)methyl]thio]-1H-benzimidazole).

EXAMPLE 2

Preparation of (Z)-5-fluoro-2-methyl-1-[[4-(methylsulfinyl)-phenyl]methylene]-1H-indene-3-acetic acid (sulindac)

(Z)-5-fluoro-2-methyl-1-[[4-(methylthio)-phenyl]methylene]-1H-indene-3-acetic acid (5 g, 14.7 mmoles) is dissolved in dichloromethane (25 ml). The solution is added with 5.4 g (14.26 mmoles) of 73% w/w phthalimidoperhexanoic acid, keeping the temperature at about 20° C. After 18 h, the solution is concentrated to a residue that is crystallized from 15 ml methanol. After drying, 4.8 g of (Z)-5-fluoro-2-methyl-1-[[4-(methylsulfinyl)-phenyl]methylene]-1H-indene-3-acetic acid (sulindac) is obtained. Molar yield: 91%.

$^1$H-NMR ($CDCl_3$): 2.21 ppm, s, 3H; 2.83 ppm, s, 3H, 3.59 ppm, s, 2H, 6.55 ppm, dt, 1H; 6.89 ppm, dd, 1H, 7.12 ppm, m, 2H, 7.68, dd, 4H.

Using the same procedure, the following compounds can be prepared:
  1-(4-fluorophenyl)-2-(4-methylsulfinyl-phenyl)-ethanone from 1-(4-fluorophenyl)-2-(4-methylthio-phenyl)-ethanone;
  (Z)-5-fluoro-2-methyl-1-[[4-(methylsulfonyl)-phenyl]methylene]-1H-indene-3-acetic acid (sulindac-sulfone) from (Z)-5-fluoro-2-methyl-1-[[4-(methylsulfinyl)-phenyl]methylene]-1H-indene-3-acetic (sulindac) acid; and
  1-(4-fluorophenyl)-2-(4-methylsulfonyl-phenyl)-ethanone from 1-(4-fluorophenyl)-2-(4-methylsulfinyl-phenyl)-ethanone.

EXAMPLE 3

Preparation of Sulindac (Z)-5-fluoro-2-methyl-1-[[4-(methylthio)-phenyl]methylene]-1H-indene-3-acetic acid (5 g, 14.7 mmoles) is dissolved in methanol (40 ml). The solution is added with 5.4 g (14.26 mmoles) of 73% w/w ε-phthalimidoperhexanoic acid, keeping the temperature at about 20° C. After 18 h, the solution is concentrated to 15 ml and cooled to 5° C. The precipitate is filtered and dried. 4.6 g of (Z)-5-fluoro-2-methyl-1-[[4-(methylsulfinyl)-phenyl]methylene]-1H-indene-3-acetic acid (sulindac) is obtained.

Molar yield: 87%.

$^1$H-NMR ($CDCl_3$): 2.21 ppm, s, 3H; 2.83 ppm, s, 3H, 3.59 ppm, s, 2H, 6.55 ppm, dt, 1H; 6.89 ppm, dd, 1H, 7.12 ppm, m, 2H, 7.68, dd, 4H.

Using the same procedure, the following compounds can be prepared:
  2-[(diphenylmethyl)sulfinyl]acetic acid from 2-[(diphenylmethyl)thio]acetic acid;
  2-[(diphenylmethyl)sulfinyl]acetamide (modafinil) from 2-[(diphenylmethyl)thio]acetamide;
  2-[(diphenylmethyl)sulfonyl]acetic acid from 2-[(diphenylmethyl)sulfinyl]acetic acid; and 2-[(diphenylmethyl)sulfonyl]acetamide (modafinil-sulfone) from 2-[(diphenylmethyl)sulfinyl]acetamide.

EXAMPLE 4

Preparation of Modafinil 10 g (38.9 mmoles) of 2-[(diphenylmethyl)thio]acetamide are dissolved in 100 ml of dichloromethane. The solution is added with 15.7 g of 68% w/w ε-phthalimidoperhexanoic acid, keeping the temperature at about 20° C., and after 6 h is diluted with water, adjusting the pH to 8–9 with aqueous ammonia. The resulting phases are separated and the organic one is evaporated to dryness, to obtain 8.5 g of 2-[(diphenylmethyl)sulfinyl]acetamide (modafinil). Molar yield: 80%.

$^1$H NMR ($CDCl_3$):

| | | | | |
|---|---|---|---|---|
| 3.22 ÷ 3.27 | ppm | d | 1H | $S(O)CH_2$ |
| 3.63 ÷ 3.68 | ppm | d | 1H (J = 12.5 Hz) | $S(O)CH_2$ |
| 5.32 | ppm | s | 1H | $S(O)CHPh_2$ |
| 7.38 ÷ 7.5 | ppm | m | 10H | Aromatic |

Using the same procedure, 2-[(diphenylmethyl)sulfinyl] acetic acid is obtained from 2-[(diphenylmethyl)thio]acetic acid.

EXAMPLE 5

Preparation of Modafinil-sulfone 10 g (38.9 mmoles) of 2-[(diphenylmethyl)thio]acetamide are dissolved in 100 ml of dichloromethane. The solution is added with 31.4 g of 68% w/w ε-phthalimidoperhexanoic acid, keeping the temperature at 20° C. and after 6 h is diluted with water, adjusting the pH to 8–9 with aqueous ammonia. The resulting phases are separated and the organic one is evaporated, to obtain 8.1 g of 2-[(diphenylmethyl)sulfonyl]acetamide (modafinil-sulfone).

Molar yield: 72%.
¹H NMR (CDCl₃):

| 3.74 | ppm | s | 2H | SO₂CH₂ |
|---|---|---|---|---|
| 5.66 | ppm | s | 1H | SO₂CHPh₂ |
| 7.26 ÷ 7.69 | ppm | m | 10H | Aromatics |

Using the same procedure, the following compounds can be prepared: 2-[(diphenylmethyl)sulfonyl]acetic acid from 2-[(diphenylmethyl)thio]acetic acid; 1-(4-fluorophenyl)-2-(4-methylsulfonyl-phenyl)-ethanone from 1-(4-fluorophenyl)-2-(4-methylthio-phenyl)-ethanone; (Z)-5-fluoro-2-methyl-1-[[4-(methylsulfonyl)-phenyl]methylene]-1H-indene-3-acetic acid from (Z)-5-fluoro-2-methyl-1-[[4-(methylthio)-phenyl]methylene]-1H-indene-3-acetic acid; and 4,4'-sulfonylbenzenamine (dapsone) from 4,4'-thiobisbenzenamine.

What is claimed is:

1. A process for the oxidation of thioethers to sulfoxides or sulfones or for the oxidation of sulfoxides to sulfones by treatment of thioethers or sulfoxides with an oxidizing amount of ε-phthalimidoperhexanoic acid in the presence of a solvent.

2. A process as claimed in claim 1, wherein a thioether is oxidized to sulfoxide and a sulfoxide is oxidized to sulfone, wherein ε-phthalimidoperhexanoic acid is used in amount ranging from 0.8 to 1.5 equivalents per equivalent of substrate.

3. A process as claimed in claim 1 wherein a thioether is oxidized to a sulfone, wherein ε-phthalimidoperhexanoic acid is used in amounts ranging from 1.5 to 3 equivalents per equivalent of substrate.

4. A process as claimed in claim 1, wherein the oxidation is carried out at a temperature ranging from −20° C. to the reflux temperature of the solvent, for a reaction time ranging from 0.5 to 24 hours.

5. A process as claimed in claim 1, wherein the oxidation is carried out in a water-miscible or immiscible, protic or aprotic organic solvent.

6. A process as claimed in claim 5, wherein the solvent is selected from aliphatic or aromatic chlorides, aromatic hydrocarbons, esters of a carboxylic acid, alkyl carbonates, alkanols, alkyl or cycloalkyl ketones, or mixtures thereof.

7. A process for the preparation of a biologically active compound containing a sulfinyl or sulfonyl group, the process comprising:
 a) oxidation of an intermediate compound containing at least one thioether to at least one sulfoxide or sulfone by treatment of the at least one thioether with an oxidizing amount of ε-phthalimidoperhexanoic acid or
 b) oxidation of an intermediate compound containing at least one sulfoxide to at least one sulfone by treatment of the at least one sulfoxide group with an oxidizing amount of ε-phthalimidoperhexanoic acid.

8. A process as claimed in claim 7, wherein the biologically active compound is selected from the group consisting of 2-[(diphenylmethyl)sulfinyl]acetamide (Modafinil); 2-[(diphenylmethyl)sulfonyl]acetamide (Modafinil-sulfone); (Z)-5-fluoro-2-methyl-1-[4-(methyl-sulfinyl)phenyl]methylene]-1H-indene-3-acetic acid (Sullndac); (Z)-5-fluoro-2-methyl-1-[(4-(methyl-sulfonyl)phenyl]methylene]-1H-indene-3-acetic acid (Sulindac-sulfone); 4,4'-sulfonylbenzenamine (Dapsone); 5-methoxy-2[[(4-methoxy-3,5-dimethyl-2-pyridinyl)methyl]sulfinyl]-1H-benzimidazole (Omeprazole); 5-difluoromethoxy-2[[3,4-dimethoxy-2-pyridinyl)methyl]sulfinyl]-1H-benzimidazole (Pantoprazole); 2-[[(methyl-4-(2,2,2-trifluoroethoxy)-2-pyridinyl]methyl]sulfinyl]-1H-benzimidazole (Lansoprazole); 2-[[(2-pyridinyl)methyl]sulfinyl]-1H-benzimidazole (T moprazole); 5-ethoxycarbonyl-6-methyl-2[[(3-methyl-2-pyridinyl)methyl]sulfinyl]-1H-benzimidazole (Picoprazole); 2-[[(3-methyl-4-(3-methoxypropoxy)-2-pyridinyl]methyl]sulfinyl]-1H-benzimidazole (Rabeprazole); (S)-5-methoxy-2[[(4-methoxy-3,5-dimethyl-2-pyridinyl)methyl]sulfinyl]-1H-benzimidazole (Exomeprazole).

9. A process as claimed in claim 7, wherein the intermediate compound containing a thioether group is selected from the group consisting of:
 1-(4-fluorophenyl)-2-(4-methylthio-phenyl)-ethanone;
 (Z)-5-fluoro-2-methyl-1-[[4-(methylthio)-phenyl]methylene]-1H-indene-3-acetic acid;
 2-[(diphenylmethyl)thio]acetic acid;
 2-[(diphenylmethyl)thio]acetamide;
 4,4'-thiobisbenzenamine;
 (5-methoxy-2[[(4-methoxy-3,5-dimethyl-2-pyridinyl)methyl]thio]-1H-benzimidazole);
 (5-difluoromethoxy)-2-[(4-chloro-3-methoxy-2-pyridinyl)methyl]thio-1H-benzimidazole;
 (5-difluoromethoxy-2[[3,4-dimethoxy-2-pyridinyl)methyl]thio]-1H-benzimidazole);
 (2-[[[methyl-4-(2,2,2-trifluoroethoxy)-2-pyridinyl]methyl]thio]-1H-benzimidazole];
 (2-[[(2-pyridinyl)methyl]thio]-1H-benzimidazole);
 (5-ethoxycarbonyl-6-methyl-2[[(3-methyl-2-pyridinyl)methyl]thio]-1H-benzimidazole);
 (2-[[[3-methyl-4-(3-methoxypropoxy)-2-pyridinyl]methyl]thio]-1H-benzimidazole); and
 (S) (5-methoxy-2[[(4-methoxy-3,5-dimethyl-2-pyridinyl)methyl]thio]-1H-benzimidazole).

10. A process as claimed in claim 9, wherein the intermediate compound containing a sulfoxide group is selected from the group consisting of (Z)-5-fluoro-2-methyl-1-[[4-(methyl-sulfinyl)phenyl]methylene]-1H-indene-3-acetic acid (Sulindac), 2-[(diphenylmethyl)sulfinyl]acetamide (Modafinil), 1-(4-fluorophenyl)-2-(4-methylsulfinyl-phenyl)-ethanone and 2-[(diphenylmethyl)sulfinyl]acetic acid.

* * * * *